United States Patent
Cho et al.

(10) Patent No.: US 10,301,591 B2
(45) Date of Patent: May 28, 2019

(54) METHOD FOR DIFFERENTIATION INTO BIOCOMPATIBLE KERATOCYTE PROGENITOR CELLS AND KERATOCYTE PROGENITOR CELL COMPOSITION

(71) Applicant: POSTECH ACADEMY-INDUSTRY FOUNDATION, Gyeongsangbuk-do (KR)

(72) Inventors: Dong-Woo Cho, Seoul (KR); Moon Nyeo Park, Gyeongsangbuk-do (KR); Sung Won Kim, Seoul (KR); Sun Hwa Park, Seoul (KR); Hyeonji Kim, Gyeongsangbuk-do (KR)

(73) Assignee: POSTECH ACADEMY-INDUSTRY FOUNDATION, Gyeongsangbuk-Do (KR)

( * ) Notice: Subject to any disclaimer, the term of this patent is extended or adjusted under 35 U.S.C. 154(b) by 341 days.

(21) Appl. No.: 15/166,695

(22) Filed: May 27, 2016

(65) Prior Publication Data
US 2017/0029773 A1  Feb. 2, 2017

(30) Foreign Application Priority Data

Jul. 30, 2015  (KR) .................... 10-2015-0108078

(51) Int. Cl.
*C12N 5/079* (2010.01)
(52) U.S. Cl.
CPC ........ *C12N 5/0621* (2013.01); *C12N 2501/11* (2013.01); *C12N 2501/117* (2013.01); *C12N 2501/119* (2013.01); *C12N 2501/15* (2013.01); *C12N 2506/1392* (2013.01)
(58) Field of Classification Search
None
See application file for complete search history.

(56) References Cited

PUBLICATIONS

Nagoshi, Narihito, et al. "Ontogeny and multipotency of neural crest-derived stem cells in mouse bone marrow, dorsal root ganglia, and whisker pad." Cell stem cell 2.4 (2008): 392-403. (Year: 2008).*
Yoshida, Satoru, et al. "Isolation of multipotent neural crest-derived stem cells from the adult mouse cornea." Stem cells 24.12 (2006): 2714-2722. (Year: 2006).*
Jakob, Mark, et al. "Human nasal mucosa contains tissue-resident immunologically responsive mesenchymal stromal cells." Stem cells and development 19.5 (2009): 635-644. (Year: 2009).*
Kim, et al., "Differentiation of Human Stem Cells into the Keratocyte Lineage In vitro on Decellularized Cornea for Corneal Tissue Engineering", Biomaterials/Bio-matrices, pp. 18-19, Sep. 30, 2014.
Park et al., "Human mesenchymal stem cells differentiate into keratocyte-like cells in keratocyte-conditioned medium," *Experimental Eye Research*, 101:16-26, 2012.
Lin Yao et al., "Review: Mesenchymal Stem Cells and Corneal Reconstruction," *Molecular Vision* 19:2237-2243 (2013).
Damien G. Harkin et al., "Concise Reviews: Can Mesenchymal Stromal Cells Differentiate into Corneal Cells? A Systematic Review of Published Data," *Stem Cells Journals*, 33(3):785-791 (2015).

* cited by examiner

*Primary Examiner* — Robert J Yamasaki
(74) *Attorney, Agent, or Firm* — Occhiuti & Rohlicek LLP

(57) ABSTRACT

Disclosed is a method for differentiation into biocompatible keratocyte progenitor cells, the method including: providing human turbinate mesenchymal stem cells (hTMSCs) from a tissue source; and culturing the provided human turbinate mesenchymal stem cells (hTMSCs) in a keratocyte differentiation medium supplemented with keratocyte growth factor (KGF), so that a differentiable keratocyte precursor cell composition that is impossible in the conventional art can be implemented, and the injection of the keratocyte progenitor cell composition into patients can produce a short-term treatment effect while securing the transparency of the cornea.

6 Claims, 5 Drawing Sheets

METHOD FOR DIFFERENTIATION INTO BIOCOMPATIBLE KERATOCYTE PROGENITOR CELLS AND KERATOCYTE PROGENITOR CELL COMPOSITION

CROSS-REFERENCE TO RELATED APPLICATIONS

This application claims the benefit of priority of Korean Patent Application No. 10-2015-0108078 filed on Jul. 30, 2015, all of which are incorporated by reference in their entirety herein.

BACKGROUND OF THE INVENTION

Field of the Invention

The present invention relates to a method for differentiation into biocompatible keratocyte progenitor cells and a keratocyte progenitor cell composition and, more specifically, to a method for differentiating stem cells into keratocyte progenitor cells and a composition therefor.

Related Art

With the development of medicine, a procedure of replacing tissues or organs, of which functions are lost due to diseases or external injury, with similar autologous tissues or organs with the same functions has been developed, but the procedure may cause a donor defect problem. Recently, in order to solve this problem, organ transplantation or tissue transplantation has been made to be replaced with tissue engineering, in which a small amount of cells are obtained from a donor, allowed to proliferate using a cell culture technique, and transplanted.

The cornea refers to the transparent membrane that covers the surface of the black pupil. The cornea performs not only a primary role of protecting eyes from the outside, but also a window role through which the eyes receive light to see things.

A structurally or functionally irreparable damage on the cornea results in bad eyesight. Moreover, corneal opacity whitens the cornea, causing a beauty problem. In order to treat this damaged cornea, tissue engineering has been attempted that a small amount of cells are obtained from a donor, allowed to proliferate using a cell culture technique, and then transplanted. Although the differentiated keratocyte progenitor cells are required to treat this corneal treatment, the differentiation of mesenchymal stem cells (MSC) into keratocyte progenitor cells is very difficult, and currently, the differentiation has not been succeeded.

SUMMARY OF THE INVENTION

The present invention has been made in view of the above-mentioned problems, and an aspect of the present invention is to provide a differentiation method capable of differentiating human turbinate mesenchymal stem cells into keratocyte progenitor cells and a differentiation-inducing composition therefor.

A method for differentiation into biocompatible keratocyte progenitor cells according to the present invention may include: providing human turbinate mesenchymal stem cells (hTMSCs) from a tissue source; and culturing the provided human turbinate mesenchymal stem cells (hTMSCs) in a keratocyte differentiation medium supplemented with keratocyte growth factor (KGF).

Furthermore, in the step of culturing in the keratocyte differentiation medium, a growth culture medium may be prepared by using a DMEM high glucose and adding 5-15% FBS and 0.5-1.5% P/S.

Furthermore, in the step of culturing in the keratocyte differentiation medium, the differentiation culture medium may be prepared by using DMEM/F12 and adding 0.5-1.5% horse serum, 8-12 ng/ml KGF, or 8-12 ng/ml EGF.

Furthermore, the method for differentiation into biocompatible keratocyte progenitor cells may include a step of cutting the isolated human turbinate tissue, allowing the turbinate tissue to adhere to the culture medium and culturing the turbinate tissue, and obtaining human turbinate mesenchymal stem cells adhering to the culture medium.

Furthermore, the method may further include a step of differentiating the human turbinate mesenchymal stem cells into keratocyte progenitor cells in the keratocyte differentiation medium.

Furthermore, the biocompatible keratocyte progenitor cell composition may be prepared by differentiating human turbinate mesenchymal stem cells (hTMSCs) in a keratocyte differentiation medium supplemented with keratocyte growth factor (KGF).

Furthermore, the composition for preventing or treating corneal damage allows corneal regeneration or corneal transplantation using the keratocyte progenitor cell composition.

Furthermore, the method for differentiation into biocompatible keratocyte progenitor cells may include a step of cutting the isolated human turbinate tissue, allowing the turbinate tissue to adhere to the culture medium and culturing the turbinate tissue, and obtaining human turbinate mesenchymal stem cells adhering to the culture medium adhering to the culture medium.

The details of other embodiments are included in the description and drawings.

The method for differentiation into biocompatible keratocyte progenitor cells and the keratocyte progenitor cells therefor according to the present invention have an advantage in that the keratocyte progenitor cell composition can be prepared using a tissue other than the corneal tissue.

Furthermore, the injection of the keratocyte progenitor cell composition according to the present invention into patients can produce a short-term treatment effect while securing the transparency of the cornea.

Furthermore, the present invention employs healthy mesenchymal stem cells (MSC), and thus can be expected to reduce the psychological burden of patients and be helpful in view of the recovery to health.

DESCRIPTION OF EXEMPLARY EMBODIMENTS

Hereinafter, the method for differentiation into biocompatible keratocyte progenitor cells and the keratocyte progenitor cells according to embodiments of the present invention will be described in detail with reference to the accompanying drawings. However, the terms or words disclosed herein are not delimited to only conventional or dictionary meanings, and should be construed to have meanings and concepts that coincide with the technical scope of the present invention on the basis of the principle that the concepts of the terms can be properly defined in order to illustrate the invention of the inventor.

Meanwhile, the configuration shown in examples and drawings of the present specification is merely one example of the present invention, and is not limited to the following examples of the present invention. Therefore, the present invention may cover not only the following examples but also various equivalents and modifications which can substitute for the examples.

Figure 1:
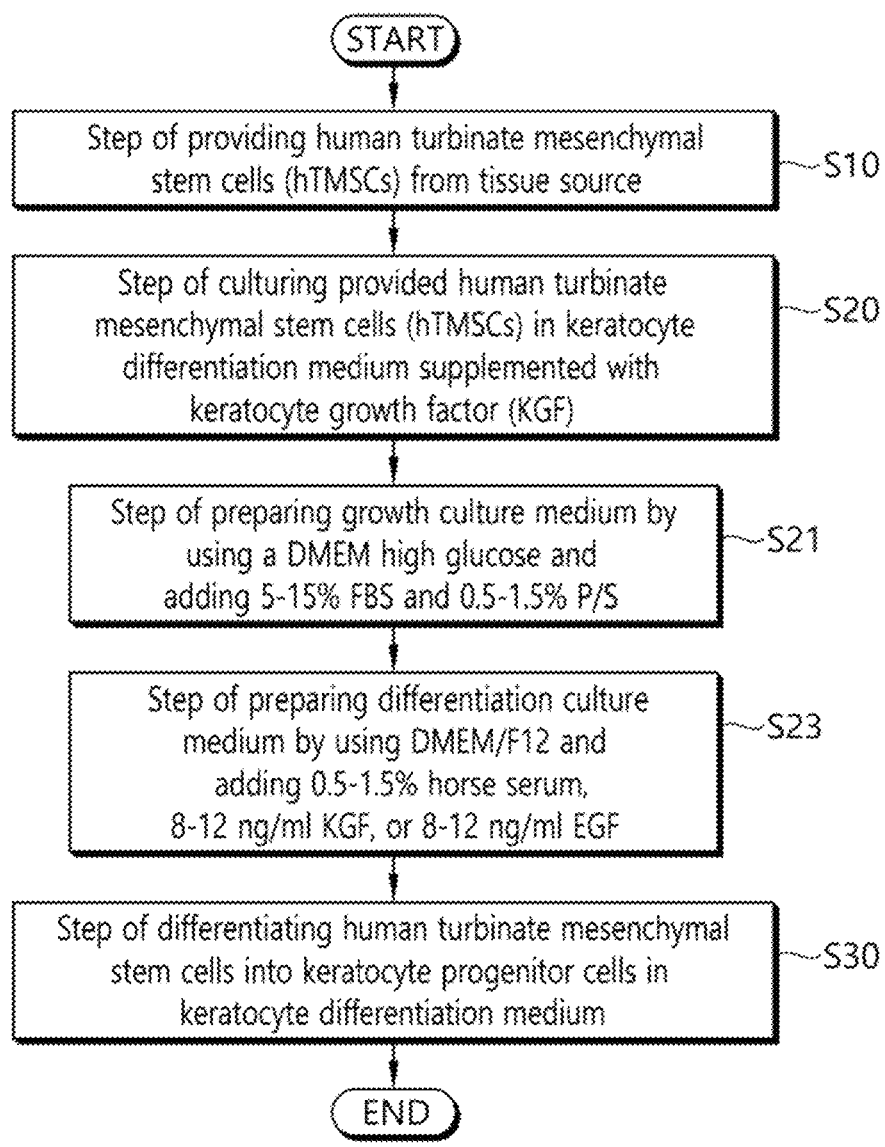
FIG. 1 is a flowchart showing a method for differentiation into biocompatible keratocyte progenitor cells according to an embodiment of the present invention.

FIG. 1 is a flowchart showing a method for inducing biocompatible keratocyte progenitor cells according to an embodiment of the present invention.

First, a step of providing mesenchymal stem cells (MSCs) is advanced (S10). Here, the human turbinate mesenchymal stem cells (hTMSCs) may be used as mesenchymal stem cells. The human inferior turbinate, which is present in the human nose, is the submucosal-rich tissue in which a large amount of net-like venous sinuses are distributed and plural mesenchymal stem cells are present around the venous sinuses.

In the present step, the tissue obtained during inferior turbinectomy may be used, or the tissue biopsied from the human body may be used. Alternatively, the turbinate mesenchymal stem cells (TMSCs) may be obtained by using various methods of isolating mesenchymal stem cells from human tissues.

For example, the turbinate mesenchymal stem cells may be obtained by fractionating the collected tissue, separating mesenchymal stem cells therefrom via density gradient centrifugation, and culturing the mesenchymal stem cells. The density gradient centrifugation is the method by which only cell fractions having a predetermined specific gravity can be obtained. When the cells are rotated for a sufficient time of period using a centrifuge, the respective cells are disposed at positions corresponding to their specific gravities, such as ficoll, percoll, and histopaque, in a centrifugal separation solution. Therefore, only mesenchymal stem cells can be obtained from the tissue in such a manner.

In addition, the human turbinate mesenchymal stem cells (hTMSCs) may be isolated by washing or cutting the provided inferior turbinate tissue, and then cultured in a medium for culturing mesenchymal stem cells. After the isolated mesenchymal stem cells are sub-cultured for 2-5 passages, and preferably 3-4 passages, the cultured mesenchymal stem cells may be used.

Besides, after the human inferior turbinate tissue is cut, the human inferior turbinate tissue per se is allowed to adhere to a culture dish, thereby removing the non-adhering cells and obtaining mesenchymal stem cells adhering to the dish.

After that, the step of culturing the provided human turbinate mesenchymal stem cells (hTMSCs) in the keratocyte differentiation medium containing at least one growth factor may be advanced (S220). Here, the cornea differentiation medium may contain a keratocyte growth factor (KGF). Through the present step, the human turbinate mesenchymal stem cells may be differentiated into keratocyte progenitor cells.

Specifically, the present step may include a step of culturing the mesenchymal stem cells in a growth culture medium (S21), and a step of differentiating the keratocyte progenitor cells in a keratocyte differentiation medium (S23). The culture medium used in the present step may be basically prepared by using a medium for culturing animal cells. For example, DMEM, α-DMEM, Eagle's basal medium, RPMI 1640 medium, neural progenitor cell basal medium (NPBM, SCIonetics), or the like may be used.

First, the growth culture medium may be provided to stabilize the cells according to an embodiment of the present invention (S21). The growth culture medium may employ DMEM high glucose and contain 5-15% FB and 0.5-1.5% P/S. For example, the growth culture medium of the present embodiment may employ DMEM high glucose and contain approximately 10% FBS and approximately 1% P/S. The mesenchymal stem cells (MSCs) were cultured in the cell growth culture medium for a day.

In addition, the mesenchymal stem cells (MSCs) are cultured in the growth culture medium for approximately one day, and then the growth culture medium is removed. In addition, the differentiation of the mesenchymal stem cells (MSCs) is induced using a new differentiation inducing culture medium. The new differentiation inducing culture medium may employ DMEMF12 and contain 0.5-1.5% horse serum and 8-12 ng/ml KGF or 8-12 ng/ml EGF. For example, the differentiation inducing culture medium of the present embodiment may employ DMEM/F12 and contain 1% horse serum and 10 ng/ml KGF or 10 ng/ml EGF. However, the present embodiment is given for one example, and the medium may be prepared to contain, as a growth factor, a fibroblast growth factor, or another growth factor, such as TGF-β3.

The corneal tissue, which is derived from the neural crest, is a sensitive tissue, which is largely composed of stroma and provided with epidermis in contact with the in vitro environment and endodermis connected to the optic nerve. Even after these keratocytes become adult keratocytes, the keratocytes have stemness characteristics. Therefore, the keratocytes are differentiated into the epidermis to repair the wound when the epidermis of the eye is wounded, and differentiated into the stroma to restore the tissue even when the stroma is wounded.

Generally, many lesions occurring in the cornea are treated in a manner in which existing corneal tissues are removed and new corneal tissues are transplanted. However, the amount of donated corneal tissues is insufficient to meet the demand of corneal transplantation, and thus the research and development for preparing corneal tissues are being advanced. Recently, tissue-engineering research for preparing these keratocytes is actively being conducted. However, although there are some successful cases of culturing corneal tissues as completely differentiated tissues, there are no cases of preparing corneal tissues including progenitor cell characteristics (having embryonic features).

Therefore, the present invention provides a method for culturing corneal tissues having progenitor cell characteristics using human turbinate mesenchymal stem cells. The human turbinate mesenchymal stem cells are highly likely to differentiate into corneal tissues since the human inferior turbinate and the cornea have the same embryonic origin (the human inferior turbinate is also derived from neural crest). In addition, the human turbinate mesenchymal stem cells can differentiate into neuronal tissues due to the multipotency thereof, and thus the human turbinate mesenchymal stem cells are suitable in the differentiation into keratocyte progenitor cells derived from neural crests. Furthermore, the human turbinate mesenchymal stem cells have excellent proliferative activity, and thus can obtain a high yield at the time of tissue culturing.

As such, in the present invention, in the differentiation into corneal tissues using human turbinate mesenchymal stem cells, the differentiation was induced using a culture medium containing at least one growth factor. Particularly, when the culture medium was prepared to contain a keratocyte growth factor as shown in the foregoing embodiment, very accurate and prompt differentiation was induced.

The extent of differentiation into keratocyte progenitor cells in the differentiation-inducing culture medium may be confirmed through a procedure in which the keratocyte progenitor cells are formed while the differentiation-inducing culture medium is exchanged every 2-3 days (S30).

Hereinafter, tests implemented to investigate the differentiation characteristics of human turbinate mesenchymal stem cells (hTMSCs) into keratocyte progenitor cells will be described.

In order to investigate whether the differentiated keratocyte progenitor cells retain desired types of features and differentiation potency, a comparative test was conducted using the keratocyte differentiation medium (KDM) according to the present embodiment and, as a control, samples cultured in the normal medium (NM).

Here, the keratocyte differentiation medium (KDM) employs DMEM/F12, and uses a solution containing 1% horse serum, 1% penicillin streptomycin (P/S), 10 ng/ml KGF/FGF-7, and 10 ng/ml EGF. In addition, the foregoing growth culture medium is used as a general culture solution for the control. The differentiation characteristics of human turbinate mesenchymal stem cells (hTMSCs) was investigated while the human turbinate mesenchymal stem cells (hTMSCs) were cultured in the foregoing two kinds of culture liquids for 1, 7, and 14 days.

Figure 2:
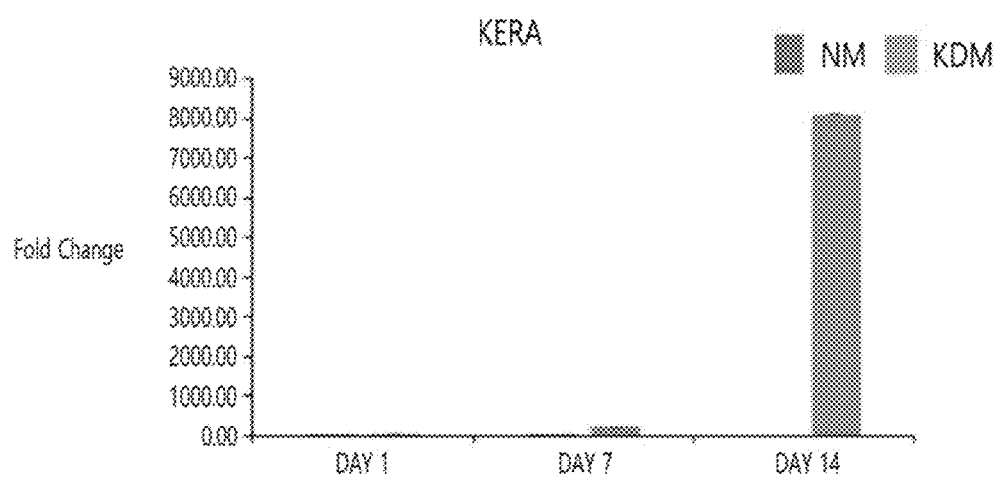
FIGS. 2 and 3 illustrate images showing genetic expression levels through the differentiation of a cell source by using human turbinate mesenchymal stem cells as the cell source and keratocyte growth factor (KGF) as a growth factor, according to an embodiment of the present invention.
Figure 2:
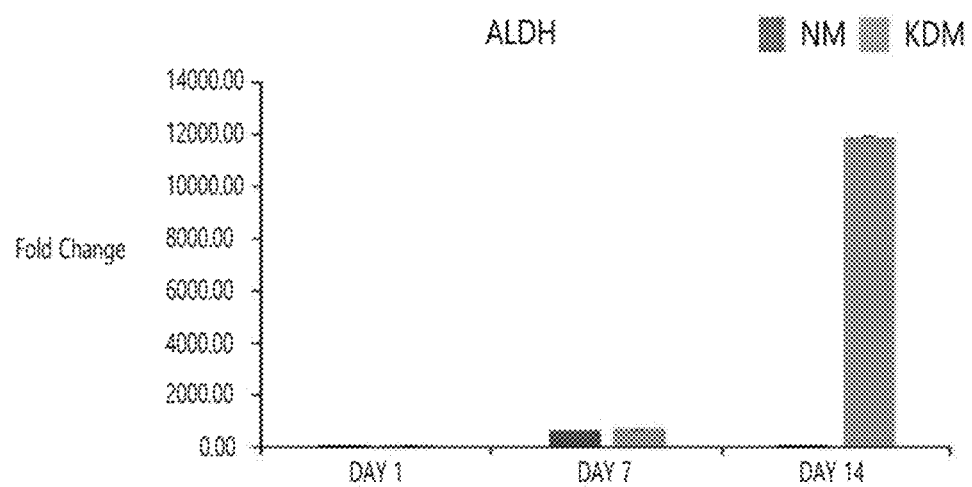
Figure 3:
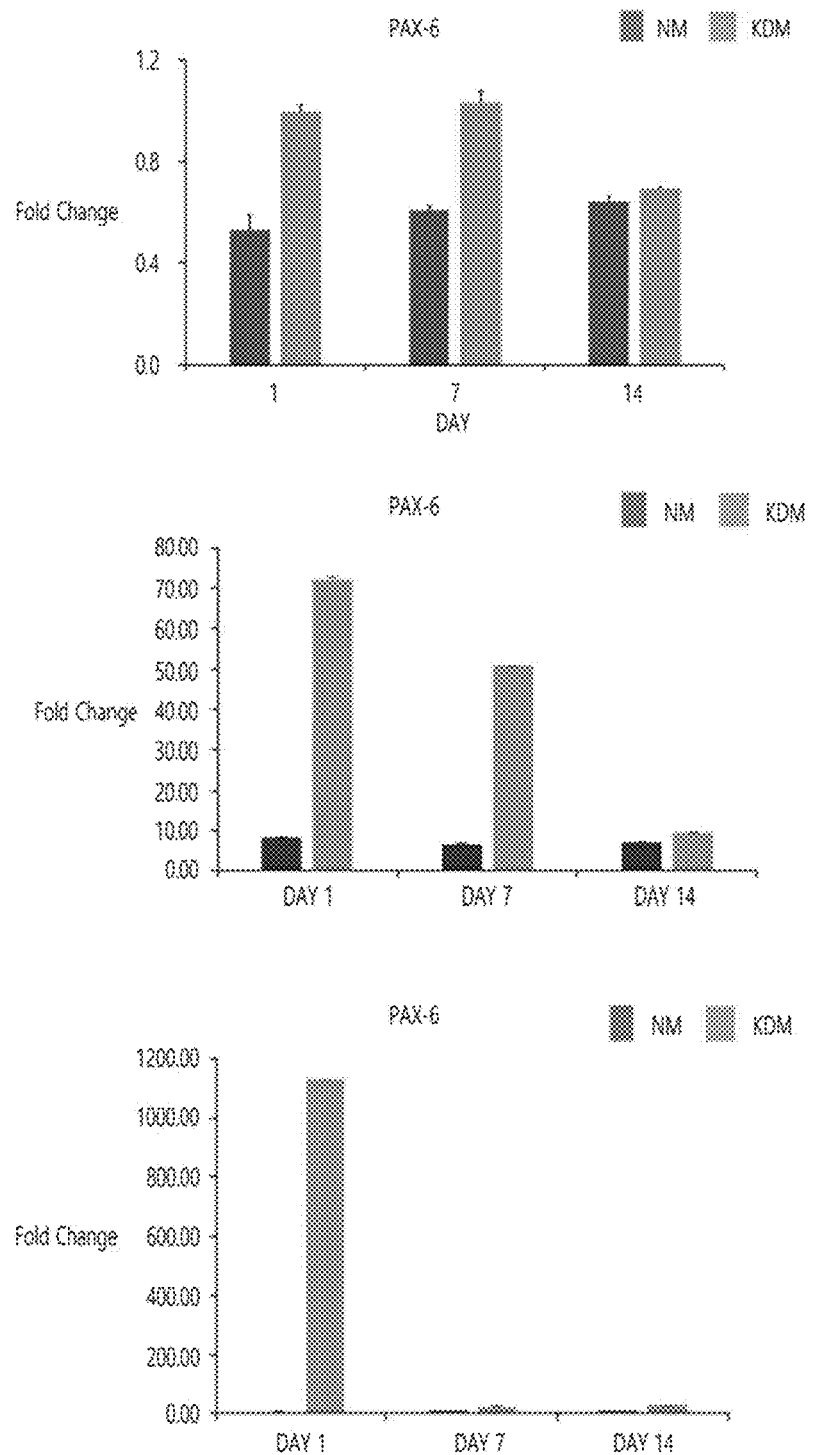

FIGS. 2 and 3 illustrate graphs showing genetic expression aspects while human turbinate mesenchymal stem cells were cultured/differentiated.

Specifically, FIG. 2 illustrates graphs showing expression characteristics of keratocan (KERA) and aldehyde dehydrogenase (ALDH), which are keratocyte expression markers; and FIG. 3 illustrates graphs showing expression characteristics of PAX-6, ABCG-2, and SOX-2, which are keratocyte progenitor cell markers.

These expression characteristics may be obtained through the PCT test. Genetic PCR primers may be prepared by inserting a site of the human keratocyte. In addition, the content of GC may be adjusted to 40-60%. In addition, the test was conducted by adding 1 ul of 20-100 pmol primers.

<Expression Aspects of Positive Markers of Keratocytes>

First, the expression levels of keratocan (KERA) and aldehyde dehydrogenase (ALDH), which are positive expression markers of keratocytes, were detected. As a result, it was verified from FIG. 2 that the expression was excellent in the cells cultured in the keratocyte differentiation culture liquid containing KGF rather than in the cells cultured in the normal culture liquid, and the expression level significantly increased over time.

That is, it was verified that turbinate mesenchymal stem cells (MSC) having multipotency differentiated to be suitable to grow to keratocytes in the culture condition according to the present embodiment. It was verified that, as for the time for differentiation, the differentiation increased over time considering that the expression level was maximal around day 14.

<Expression Aspects of Progenitor Markers>

In addition, expression levels of PAX-6, ABCG-2, and SOX-2, which are progenitor cell markers, were detected. As a result, as shown in FIG. 3, the expression levels were high in the cells cultured in the keratocyte differentiation culture liquid containing KGF rather than in the cells cultured in the normal culture liquid. In addition, the characteristics as progenitor cells, in which the expression level is large at the initial stage of differentiation, and the expression level is reduced at the terminal stage of differentiation, were shown similarly.

Especially, in the present embodiment, both of PAX-6 and ABCG-2 were expressed. Here, PAX-6 is a marker of stroma-related progenitor cells, ABCG-2 is a marker of epidermis-related progenitor cells, and SOX-2 is a marker of endodermis-related progenitor cells. Therefore, the inclusion of these progenitor cell markers means that the tissue cultured in the present embodiment can differentiate into the corneal epidermis, the corneal stroma, and the corneal endodermis, while being transplanted.

In consideration of the conventional studies, it was first established that all of these progenitor cell markers are expressed, and thus the present embodiment provides a method for effectively differentiating the mesenchymal stem cells into keratocyte differentiation progenitor cells. In addition, while the method of isolating keratocyte differentiation progenitor cells from the corneal tissue is very difficult and produce a small amount of gain, the present embodiment can easily obtain keratocyte differentiation progenitor cells through the differentiation of mesenchymal stem cells.

<Protein Expression Aspects of Main Markers>

Figure 4:
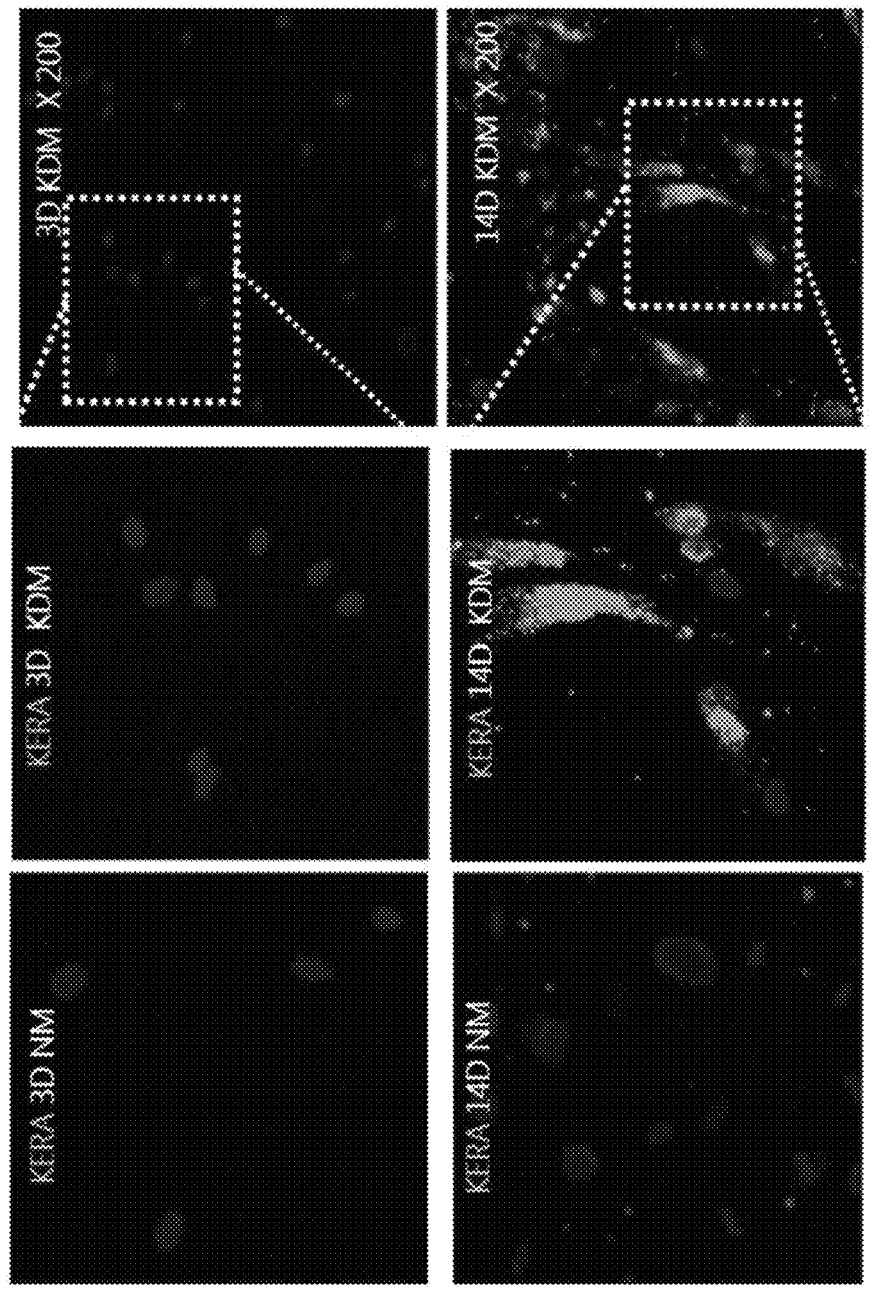
FIGS. 4 and 5 illustrate images showing gene and protein expression levels of main markers in FIGS. 2 and 3.
Figure 5:
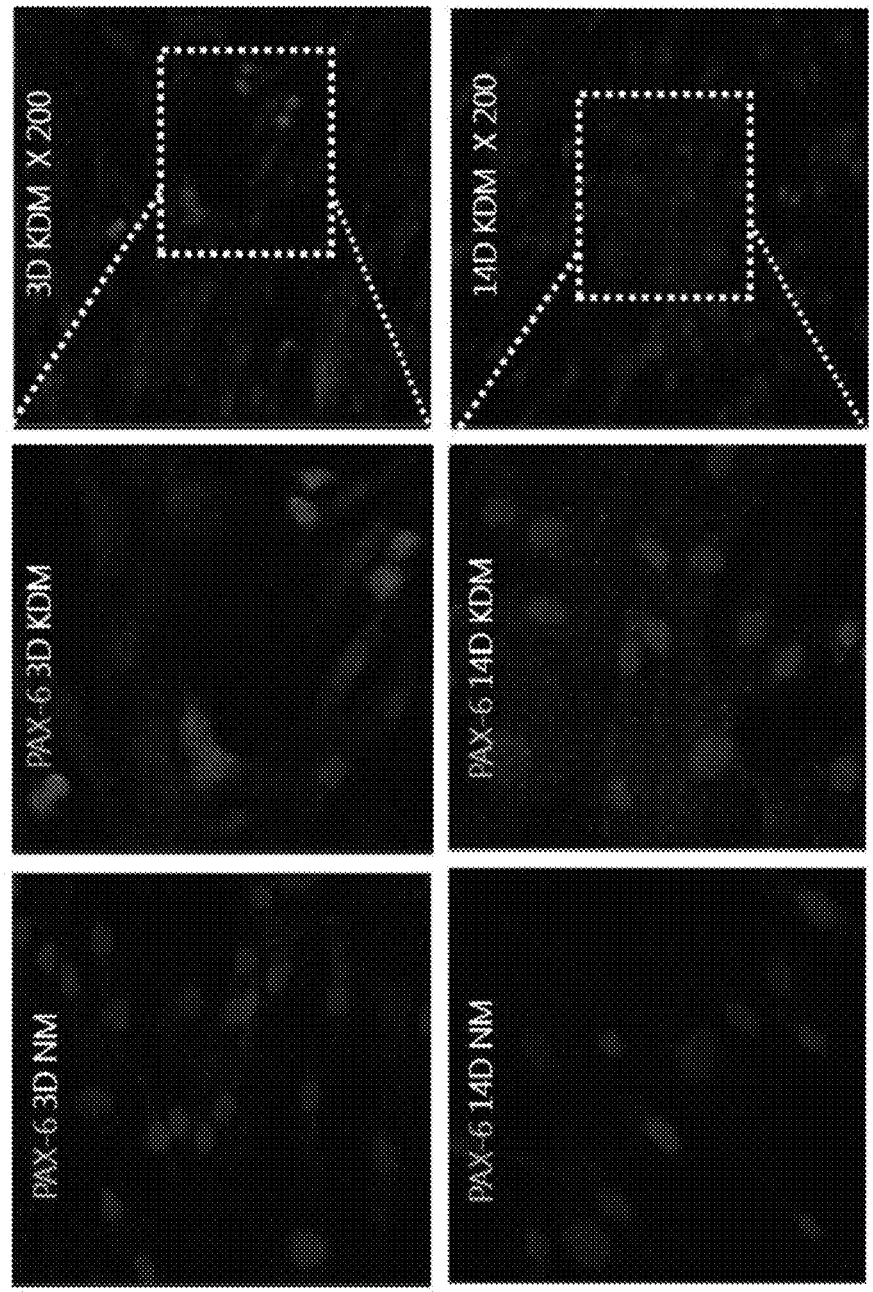

Meanwhile, FIGS. 4 and 5 illustrate immunostaining images for investigating protein expression levels of main markers. Specifically, FIG. 4 is an immunostaining image of keratocan (KERA), which is a keratocyte expression marker, and FIG. 5 is an immunostaining image of PAX-6, which is a progenitor cell marker.

The present test is to investigate protein expression levels according to the differentiation method of the present embodiment. Samples obtained by differentiation of human turbinate mesenchymal stem cells in the keratocyte differentiation culture liquid and the normal culture liquid for 3 days and 14 days, respectively were photographed.

As shown in FIG. 4, it was verified that the protein expression of KERA occurred in the cytoplasm, and the expression level significantly increased over time in the conditions of differentiation in the keratocyte differentiation culture liquid. In addition, the expression characteristics similar to the genetic expression of KERA shown in FIG. 2 were verified.

In addition, as shown in FIG. 5, it was verified that the protein expression of PAX-6 occurred in the nucleus, and the expression occurred along the surroundings of the stained nucleus in the conditions of differentiation in the keratocyte differentiation culture liquid. Here, it was verified that the expression level was relatively high at the initial stage of differentiation and the expression level was reduced at the termination stage of differentiation. Therefore, the expression characteristics similar to the genetic expression of PAX-6 shown in FIG. 3 were verified.

<Verification of Change in Multipotent Characteristics of hTMSCs after Differentiation into Keratocyte Progenitor Cells>

In order to verify whether there is a change in multipotent characteristics of human turbinate mesenchymal stem cells (hTMSCs) during or after the differentiation into keratocyte progenitor cells, the expression levels of multipotent markers expressed on the surface of the human turbinate mesenchymal stem cells were investigated through FACS assay. In addition, the expression of PAX6, a precursor cell marker, which is expected to relatively increase during the differentiation, was also investigated.

The cells differentiating into keratocyte progenitor cells and the control cells were collected on days 1, 3, 7, 14, and 21, respectively, and then FACS assay was conducted using antibodies, which are, respectively, specific to i) CD14, CD19, CD34, and CD29, which are hematopoietic lineage negative phenotype markers, ii) CD73, CD90, and CD105, which are mesenchymal stem cell positive phenotype markers, iii) HLA-DR, which is a negative phenotype marker of an immune rejection response, and iv) PAX6, which is a progenitor cell phenotype marker, among immune phenotype markers of turbinate mesenchymal stem cells (TMSCs).

Through the present test, it was verified that keratocyte specific genes were expressed most frequently on days 7 and 14.

The above results could confirmed that the differentiation of the turbinate mesenchymal stem cells were well induced and thus expressed as keratocyte progenitor cells in the medium containing KGF. Also, the position and aspect of cell expression, which are the most characteristics of keratocyte progenitor cells, were confirmed through PAX6 staining.

It was verified through the above test that the differentiation into keratocyte progenitor cells was conducted by confirming the expression of genes associated with the main functions of keratocytes. In addition, it was confirmed that the differentiated turbinate MSCs had a dendritic shape, as a feature of keratocytes, which is different from that of the control.

In conclusion, it was confirmed in the present invention that the differentiation into multipotent keratocyte progenitor cells for allowing the regeneration of the corneal epidermis, stroma, and endodermis, which play the most important roles after corneal transplantation, can be achieved, by using human turbinate mesenchymal stem cells (hTMSCs), which are derived from the neural crest having the same embryonic development stage as keratocytes, corresponding to an important issue in the corneal transplantation, and keratocyte growth factor (KGF) as a growth factor. In addition, it was verified that the expression of the most important gene involved in the corneal transparency can be induced, and the fears of immune rejection at the time of corneal transplantation can be eliminated, that is, the fears of the immune rejection response due to auto-transplantation can be eliminated, thereby suggesting the possibility as a novel therapeutic agent for corneal regeneration.

According to the present embodiments, considering that the expression of the progenitor cells is the highest within 7 days after culturing, it is possible to perform auto-transplantation within one week by using patient's tissue. Such a case produce more favorable effects in the corneal treatment on the patient compared with cases where the cells isolated from the dead body are transplanted or different species of cells are transplanted, and the inferior turbinectomy can be easily performed in the otorhinolaryngology field. The obtained cells have a remarkably favorable proliferation, and thus the necessary number of cells can be obtained within a short time. Furthermore, the psychologically stable treatment can give compared with when cells are isolated from the other eye of the patient.

Although the embodiments of the present invention has been described with reference to the accompanying drawings, a person skilled in the art to which the present invention pertains should apprehend that the present invention can be embodied in other specific forms without departing from the technical spirit or essential characteristics thereof. Therefore, the embodiments described above should be construed as as being exemplified and not limiting the present disclosure. The scope of the present invention is not defined by the detailed description as set forth above but by the accompanying claims of the invention, and it should also be understood that all changes or modifications derived from the definitions and scopes of the claims and their equivalents fall within the scope of the invention.

What is claimed is:

1. A method for preparing a biocompatible corneal tissue, the method comprising:
    obtaining mesenchymal stem cells from a non-corneal neural crest derived tissue wherein the obtained mesenchymal stem cells are human turbinate mesenchymal stem cells; and
    culturing the obtained mesenchymal stem cells into a corneal tissue in a culture medium containing at least one growth factor, wherein the corneal tissue comprises keratocyte progenitor cells expressing at least two markers selected from PAX-6, ABCG-2, and SOX-2.

2. The method of claim 1, wherein the step of culturing into the corneal tissue, comprises:
    growing the obtained mesenchymal stem cells in a growth culture medium; and
    differentiating the mesenchymal stem cells, which have been cultured in the growth culture medium, in a keratocyte differentiation medium.

3. The method of claim 2, wherein the growth culture medium employs DMEM high glucose and contains 5-15% fetal bovine serum (FBS) and 0.5-1.5% penicillin/streptomycin (P/S).

4. The method of claim 3, wherein the keratocyte differentiation medium employs DMEM/F12 and contains 0.5-1.5% horse serum, and 8-12 ng/ml keratocyte growth factor (KGF) or epidermal growth factor (EGF).

5. The method of claim 1, wherein the keratocyte progenitor cells are differentiable into at least two of corneal epidermis, stroma, and endodermis.

6. A cell differentiation method, comprising:
    obtaining mesenchymal stem cells from a non-corneal neural crest derived tissue, wherein the obtained mesenchymal stem cells are human turbinate mesenchymal stem cells; and
    differentiating the obtained mesenchymal stem cells into keratocyte progenitor cells in a culture medium containing at least one growth factor, wherein the keratocyte progenitor cells express at least two markers selected from PAX-6, ABCG-2, and SOX-2.

* * * * *